United States Patent [19]

Wall

[11] Patent Number: 5,609,751
[45] Date of Patent: Mar. 11, 1997

[54] PARA-XYLENE SELECTIVE REFORMING/AROMATIZATION

[75] Inventor: Robert G. Wall, Pinole, Calif.

[73] Assignee: Chevron Chemical Company, San Ramon, Calif.

[21] Appl. No.: 280,279

[22] Filed: Jul. 26, 1994

[51] Int. Cl.$^6$ .................................................. C10G 35/09
[52] U.S. Cl. ...................... 208/133; 208/135; 208/137; 208/138
[58] Field of Search .................................. 208/133, 135, 208/137, 138

[56] References Cited

U.S. PATENT DOCUMENTS

| | | | |
|---|---|---|---|
| 4,007,231 | 2/1977 | Butter . | |
| 4,097,543 | 6/1978 | Haag et al. . | |
| 4,101,595 | 7/1978 | Chen et al. | 260/668 A |
| 4,117,026 | 9/1978 | Haag et al. . | |
| 4,118,429 | 10/1978 | Fritsch et al. | 208/143 |
| 4,375,573 | 3/1983 | Young | 585/467 |
| 4,443,326 | 4/1984 | Field | 208/138 |
| 4,469,909 | 9/1984 | Chester et al. | 585/483 |
| 4,560,820 | 12/1985 | Field | 585/486 |
| 5,028,573 | 7/1991 | Brown | 505/482 |
| 5,082,984 | 1/1992 | Brown et al. | 585/481 |

*Primary Examiner*—Helanc Myers
*Attorney, Agent, or Firm*—Fliesler, Dubb, Meyer & Lovejoy

[57] ABSTRACT

An intermediate pore size molecular sieve supported catalyst includes a platinum group component and a gallium, zinc, indium, iron, tin or boron component. It is used for reforming and aromatization during which it produces a paraxylene enriched product. It comprises an intermediate pore size molecular sieve support, a platinum group component and a component selected from the group consisting of gallium, zinc, indium, iron, tin or boron. One form of the catalyst is first coked and is then contacted with hydrogen. The catalyst is useful in reforming and aromatizing operations.

18 Claims, 2 Drawing Sheets

PARA-XYLENE SELECTIVE REFORMING/AROMATIZATION

TECHNICAL FIELD

The present invention relates to a unique reforming or aromatization process for producing $C_8$ aromatics which are enriched to above equilibrium levels in para-xylene from feeds containing $C_8$ non-aromatics, the catalyst used in such a process and the methods of forming the catalyst.

BACKGROUND OF THE INVENTION

Para-xylene is useful for the production of terephthalic acid. Terephthalic acid is used for the production of polyester resins and fibers such as Dacron. Para-xylene is a byproduct of reforming processes for the manufacture of fuels, particularly for the manufacture of gasoline. Paraxylene occurs in approximately equilibrium amounts, about 22%, in the $C_8$ aromatics fraction of a typical reformate stream. (All %s mentioned herein are weight %s.)

Para-xylene and other aromatics can be recovered from reformates using a combination of extraction and distillation steps. Para-xylene can be separated from other $C_8$ aromatics and purified by processes which include crystallization or adsorption processes. The other $C_8$ aromatics, which now contain para-xylene in less than equilibrium amounts, are typically recycled through an isomerization unit in order to bring the para-xylene percentage back up to near equilibrium levels. The resulting stream is then recycled to the separation and purification unit to recover additional para-xylene.

The efficiency of para-xylene recovery and purification would be increased and the cost would be decreased if the $C_8$ aromatics feedstream was enriched in para-xylene. In the best case, with a very rich para-xylene stream, the recycle through the isomerization step could be eliminated entirely. Since conventional reforming and aromatization produces para-xylene at only approximately equilibrium levels a conventional reforming or aromatization process does not give the desired improved efficiency of para-xylene recovery. A reforming/aromatization catalyst and process which would give $C_8$ aromatics which are enriched in para-xylene above equilibrium levels would thus be highly desirable.

It is known to produce xylenes with paraxylene levels above equilibrium by disproportionation of toluene. This process produces xylenes and benzene by a transalkylation mechanism. Patents which illustrate the production of paraxylene rich xylene streams from the disproportionation of toluene include U.S. Pat. Nos. 4,011,276; 4,016,219; 4,052,476; 4,029,716; 4,067,919; 4,097,543; 4,098,837; 4,127,616; 4,160,788; 4,182,923; 4,361,713; 4,365,104; 4,367,359; 4,370,508; 4,308,685 and 4,384,155, all of which are incorporated by reference.

U.S. Pat. No. 4,007,231 discloses the use of an antimony oxide modified zeolite, for example, HZSM-5, to produce para-xylene rich $C_8$ aromatics from toluene and from $C_3$–$C_{10}$ paraffins, olefins, or naphthenes. Also, U.S. Pat. No. 4,117,026 utilizes an intermediate pore zeolite, for example, HZSM-5, which has been modified by metal oxides, precoking or using a large crystal form to produce para-xylene rich $C_8$ aromatics from toluene or high molecular weight olefinic or paraffinic feeds. In this patent a dodecane feed shows 63% para-xylene enrichment of the $C_8$ aromatics. The catalyst does not contain a platinum group component and is not utilized for processing a $C_5$–$C_9$ predominantly paraffinic/olefinic hydrocarbon feedstock.

Some catalysts are known to be shape selective for the isomerization of ethylbenzene into para-xylene rich xylenes. Isomerization catalysts and process of this nature are set forth in U.S. Pat. No. 4,101,595; 5,028,573; 5,082,984; 4,783,571 and 5,043,512.

None of the prior art is concerned with an aromatization process or a reforming process which will produce acceptably high yields of para-xylene rich xylenes starting with a $C_8$ non-aromatics containing feed such as a typical reformer feedstock.

DISCLOSURE OF INVENTION

The present invention is directed to overcoming one or more of the problems as set forth above.

In accordance with an embodiment of the present invention a method is set forth of reforming or aromatizing a $C_5$–$C_9$ predominantly paraffinic or olefinic hydrocarbon feedstock containing $C_8$ non-aromatics to produce a product stream which is enriched in para-xylene. The feedstock is contacted under reforming or aromatization conditions with a catalyst which comprises an intermediate pore size molecular sieve support, a platinum group component and a component selected from the group consisting of gallium, zinc, indium, iron, tin and boron. The catalyst is capable of converting a paraffinic feed in a reforming or aromatization operation under reforming or aromatization conditions to a product which includes xylenes which are enriched in para-xylene. The catalyst has an activity sufficient to produce a yield of benzene-toluene-xylenes-ethyl benzene (BTX) of at least about 30% from the feedstock, based on the $C_6$–$C_8$ non-aromatics content of the feedstock, on a hydrogen free basis. At least about 15% of the BTX consists of xylenes with the xylenes being at least about 30% para-xylene.

In accordance with another embodiment of the present invention a catalyst is set forth which is useful for reforming and aromatization and which comprises an intermediate pore size molecular sieve support, a platinum group component and a component selected from the group consisting of gallium, zinc, indium, iron, tin and boron. The catalyst is capable of converting a predominantly paraffinic or olefinic feed in a reforming or aromatization operation under reforming or aromatization conditions to a product which includes xylenes which are enriched in paraxylene. The catalyst has an activity sufficient to produce a yield of benzene-toluene-xylenes-ethyl benzene (BTX) from a hydrocarbon feedstock containing $C_6$–$C_8$ non-aromatics of at least about 30%, based on the $C_6$–$C_8$ non-aromatics content of the feedstock on a hydrogen free basis. At least about 15% of the BTX consists of xylenes with the xylenes being at least about 30% para-xylene.

In accordance with still another embodiment of the present invention a method is set forth of producing a catalyst having an activity under reforming or aromatization conditions as set forth above. The method comprises contacting a catalyst comprising an intermediate pore size molecular sieve support, a platinum group component and a component selected from the group consisting of gallium, zinc, indium, iron, tin and boron with a hydrocarbon feedstock until the catalyst becomes coated with coke sufficiently so that it is capable of converting toluene by disproportionation to xylenes which are rich in para-xylene. The catalyst, prior to the contacting, is capable of converting an n-octane feed to products other than n-octane at a temperature of 500° C., a liquid hourly space velocity of 0.5 to 10, a pressure of 0 to 800 psig and a hydrogen to hydrocarbon molar ratio within the range from 1:1 to 20:1. The coked catalyst is exposed to a hydrogen atmosphere for a time sufficient so that, following such exposure, it is capable of converting at least 30% of an n-octane feed to products other than noctane at a temperature of 500° C., a liquid hourly space velocity of 0.5, a pressure of 75 psig and a hydrogen to hydrocarbon molar ratio of 10:1.

A large number of molecular sieves are known to have use as catalysts in various hydrocarbon conversion reactions such as disproportionation, aromatization including reforming, catalytic cracking, hydrocracking, dehydrocyclization, isomerization and dewaxing. Typical intermediate pore size molecular sieves of this nature include ZSM-5, silicalite, generally considered to be a high silica to alumina ratio form of ZSM-5, ZSM-11, ZSM-22, ZSM-23, ZSM-35, SSZ-32, SAPO-11, SAPO-31, SAPO-41, and the like. Zeolites such as ZSM-5, ZSM-11, ZSM-12, ZSM-23, ZSM-35 and ZSM-38 are described in U.S. Pat. Nos. 3,700,585; 3,894,938; 3,849,290; 3,950,241; 4,032,431; 4,141,859 4,176,050; 4,181,598; 4,222,855; 4,229,282; and 4,247,388 and in British Patent 1,469,345. The use of such catalysts, particularly para-selective forms of such catalysts which contain a platinum group aromatization promoting component, for the production of para-xylene enriched xylene products from a hydrocarbon, generally paraffinic feedstock, is not known and has generally not been contemplated.

Operating in accordance with the present invention one can begin with a typical primarily non-aromatic reformer feed, for example a $C_5$–$C_9$ feed with about a 300° F. end point, and reform the feed to form a product which contains para-xylene in above equilibrium amounts. The $C_5$–$C_9$ feed can also contain minor amounts of $C_{10}$+ components. Generally at least about 30% of the $C_8$ aromatics will be in the form of para-xylene. The BTX fraction of the feed can be separated, for example by distillation, and utilized to produce benzene, toluene and xylenes, particularly para-xylene, which can then be utilized in chemical synthesis. The remainder of the reformate will generally be useful as a gasoline blending stock. This result is particularly surprising since, as will be demonstrated below, if one starts with a pure n-heptane ($C_7$) feed under the same conditions, the resulting product, while it contains substantial amounts of toluene and a $C_8$ aromatics fraction which is enriched in para-xylene, contains so little xylenes whereby the process would be highly inefficient in the manufacture of para-xylene. This indicates that what is occurring is not reforming to form toluene followed by disproportionation of the toluene to form benzene and a para-xylene rich xylene fraction, but rather direct conversion of the paraffins in the feed, and apparently of lower molecular weight paraffins as well, to xylenes which are enriched in para-xylene. It is also surprising and unexpected that a catalyst which has been selectivated for producing para-xylene enriched xylenes by disproportionation of toluene and in which is included a platinum group component would have sufficient reforming/ aromatization activity to produce acceptable yields of aromatics.

BRIEF DESCRIPTION OF DRAWINGS

The invention will be better understood by reference to the figures of the Drawings, wherein.

DETAILED DESCRIPTION OF THE INVENTION

Figure 1:
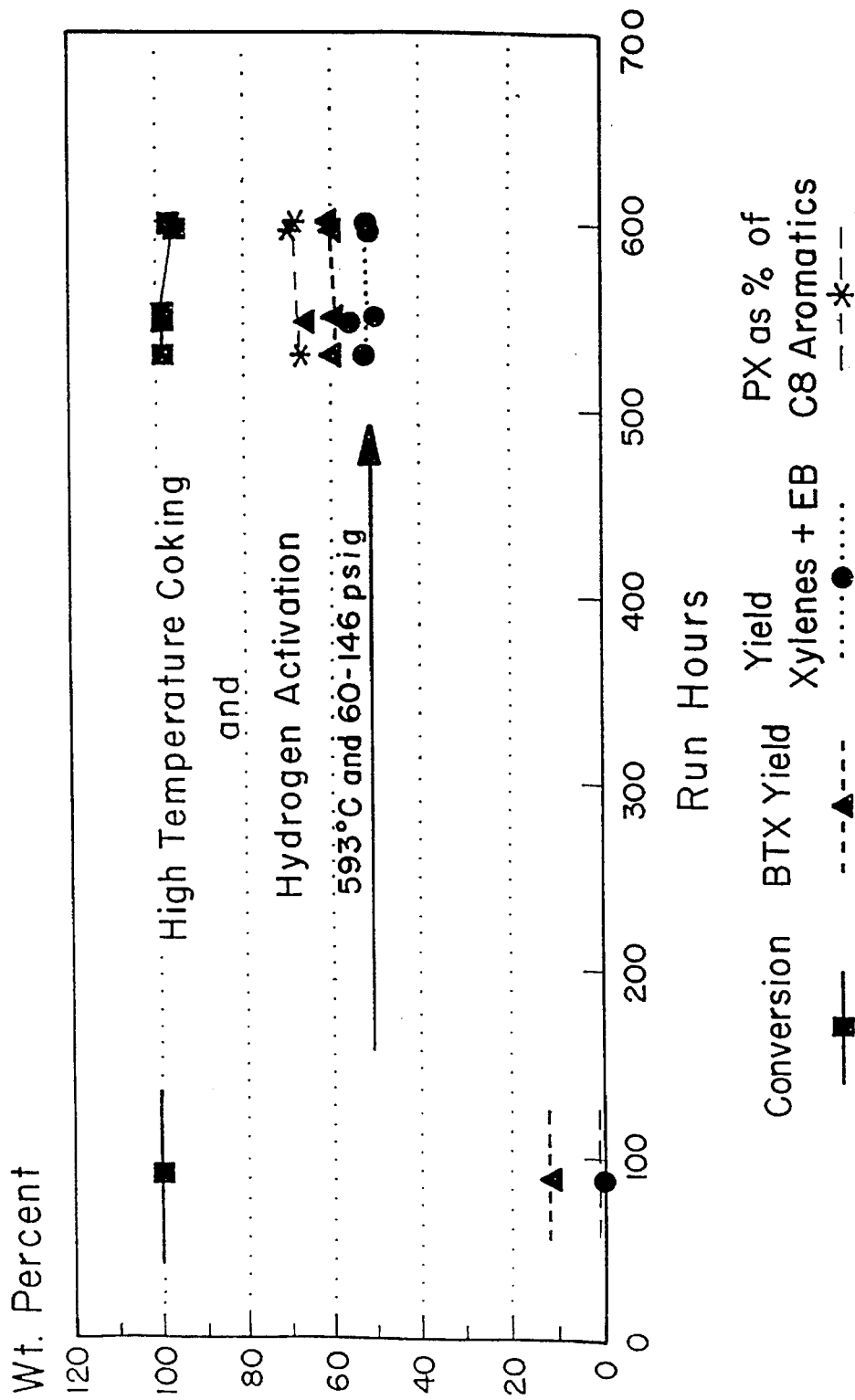
FIG. 1 illustrates experimental results as described in Example 7.

A novel catalyst useful for reforming and/or aromatization forms one aspect of the present invention. The catalyst comprises an intermediate pore size molecular sieve support, a platinum group component and a component selected from the group consisting of gallium, zinc, indium, iron, tin, boron, and mixtures thereof.

Zeolites can be characterized by their absorption characteristics at relatively low temperatures, for example from 77° K. to 420° K., as described in, for example, Zeolite Molecular Sieves, Donald W. Breck, First Edition, John Wiley & Sons, 1974. These absorption characteristics are a function of the kinetic diameters of the particular molecule being absorbed and of the channel dimensions of the molecular sieve. Intermediate pore size molecular sieves useful in the practice of the invention in the H-form will typically admit molecules having kinetic diameters of 5.0 to 6.0 Å with little hindrance. Examples of such compounds (and their kinetic diameters in Å) are: n-hexane (4.3), 3-methylpentan (5.5), benzene (5.8), and toluene (5.8). Compounds having kinetic diameters of about 6.0 to 6.8 Å can be admitted into the pores, depending on the particular sieve, but do not penetrate as quickly and in some cases are effectively excluded. Compounds having kinetic diameters in the range of 6.0 to 6.8 Å include: cyclohexane (6.0), 2,3-dimethylbutane (6.1), 2,2-dimethylbutane (6.2), m-xylene (6.1) 1,2,3,4-tetramethylbenzene (6.4) and o-xylene (6.8). Generally, compounds having kinetic diameters of greater than about 6.8 Å do not penetrate the pore apertures and thus are not absorbed into the interior of the molecular sieve lattice. Examples of such larger compounds include: hexamethylbenzene (7.1), 1,3,5-trimethylbenzene (7.5), and tributylamine (8.1).

Specific molecular sieves which are useful in the process of the present invention include the zeolites ZSM-5, ZSM-11, ZSM-12, ZSM-21, ZSM-22, ZSM-23, ZSM-35, ZSM-38, ZSM-48, ZSM-57, SSZ-23, SSZ-25, SSZ-32, and other molecular sieve materials based upon aluminum and/or magnesium phosphates such as SAPO-11, SAPO-31, SAPO-41, MAPO-11 and MAPO-31. Such molecular sieves are described in the following publications, each of which is incorporated herein by reference: U.S. Pat. Nos. 3,702,886; 3,709,979; 3,832,449; 3,950,496; 3,972,983; 4,076,842; 4,016,245; 4,046,859; 4,234,231; 4,440,871 and U.S. patent applications Ser. Nos. 172,730 filed Mar. 23, 1988 and 433,382, filed Oct. 24, 1989. In most cases, these molecular sieves must be further treated to impart para-selectivity as discussed below.

The sieves are preferably bound with any of a variety of well-known inorganic oxide binders. Appropriate binders include inorganic compositions with which the molecular sieve can be combined, dispersed or otherwise intimately admixed. Preferred oxide binders include alumina, silica, naturally occurring and conventionally processed clays, for example, bentonire, kaolin, sepiolite, attapulgite and halloysite.

The catalysts according to the present invention contain one or more platinum group metals, preferably iridium, palladium, and most preferably platinum. They are quite selective with regard to aromatization via dehydrocyclization and are also very stable under the dehydrocyclization reaction conditions. The preferred percentage of the platinum group metals, such as platinum, in the catalyst is between 0.1 wt. % and 5 wt. %, more preferably from 0.3 wt. % to 2.5 wt. %.

Platinum group metals are preferably introduced into the crystalline silicate by impregnation, occlusion, or exchange in an aqueous solution of an appropriate salt. When it is desired to introduce two platinum group metals, or a platinum group metal along with another metal such as gallium, zinc or indium, into the crystalline silicate, the operation may be carried out simultaneously or sequentially. Preferably, the platinum group metal is finely dispersed within, and on, the crystalline silicate.

By way of example, platinum can be introduced by impregnation with an aqueous solution of tetraammineplatinum (II) nitrate, tetraammineplatinum (II) hydroxide, dinitrodiamino-platinum or tetraammineplatinum (II) chloride. In an ion exchange process, platinum can be introduced by using cationic platinum complexes such as tetraammineplatinum (II) nitrate. When platinum is introduced into the silicate by occlusion a platinum complex is preferably introduced into the crystalline silicate during its formation.

The other component of the catalyst is a component selected from the group consisting of gallium, zinc, indium, iron, tin and boron. This component serves the purpose of increasing the yield of aromatics in the aromatization or reforming process. As described by P. Meriaudeeau, G. Sapaly, and C. Naccache in the Journal of Molecular Catalysts, 81 (1993) 293–300, Ga may play several roles. Replacing Al by Ga in the framework of ZSM-5 can modify catalytic activity by reducing the catalyst acidity (C. T. W. Chu and C. D. Chang, J. Phys. Chem. 89 (1995) 1569) and non-framework Ga may impart dehydrogenation activity to the catalyst (D. K. Simmons, R. Szostak, P. K. Agraval, and T. L. Thomas, J. Catalysis 106 (1987) 287). As described by E. Iglesia, J. E. Baumgartner, and G. L. Price in the J. Catalysis 134 (1992) 549–571, Ga may promote dehydrogenation by facilitating H atom recombination to give $H_2$. The gallium, indium, zinc, iron, tin and boron may be functioning by any or all of the above mentioned roles or by other yet to be discovered roles which serve to increase aromatics yields.

The Ga may be introduced into the catalyst by any suitable method such as impregnation, ion exchange, or by using a Ga source in place of Al in the preparation of the zeolite structure. The preferred method is by substitution of Ga for Al in the preparation of the zeolite. For example, a Ga ZSM-5 with Ga in the framework can be prepared by the procedure of D. K. Simmons, R. Szostak, P. K. Agraval and T. L. Thomas as described in the Journal of catalysis, 106 (1987), 287. A framework Ga ZSM-5 may also be prepared by using a Ga salt in place of the Al in the procedure for producing ZSM-5 as described in U.S. Pat. No. 3,703,886, issued April 14, 1967 to R. J. Argauer and G. R. Landolt. Ga may be impregnated onto the ZSM-5 zeolite by the procedure of U.S. Pat. No. 4,174,057, issued Nov. 20, 1979 to E. E. Davies and A. J. Kolombos which is incorporated herein by reference. Ga may also be exchanged or impregnated into the zeolite by the procedure of U.S. Pat. No. 4,891,463, issued Jan. 2, 1990 to C. T-W Chu which is incorporated herein by reference. In all of these methods there is potential for the Ga to occupy both framework and non-framework sites in the working catalyst. The preferred method gives a predominance of the Ga in the framework of the freshly prepared Ga ZSM-5. However, in the working form of the Ga ZSM-5, the Ga may occupy both framework and non-framework sites.

Zinc can be introduced into the catalyst in the manner set forth in U.S. Pat. No. 4,720,602 issued Jan. 19, 1988 to C. T-W. Chu, which patent is hereby incorporated herein by reference.

Indium can be introduced into the catalyst in the manner set forth in U.S. Pat. No. 4,822,942, issued Apr. 18, 1989 to Ralph M. Dessau and Ernest W. Valyocsik, which patent is hereby incorporated herein by reference. The Indium may also be introduced by standard impregnation or ion exchange methods.

Iron can be introduced into the catalyst in the manner set forth in U.S. Pat. No. 4,665,255, issued May 12, 1987 to Clarence D. Cheng and Joseph N. Miale, which is incorporated herein by reference. The iron may also be introduced by conventional impregnation or ion exchange methods.

A borosilicate zeolite of intermediate pore structure can be synthesized by the procedure set forth in U.S. Pat. No. 5,187,132, issued Feb. 16, 1993 to Stacey I. Zones, et al, which is incorporated herein by reference.

Tin may be introduced into the catalyst using a tin salt such as stannous chloride or acetate in conventional impregnation or ion exchange methods.

The preferred component is gallium. The gallium, zinc, indium, iron, tin or boron is generally present in an amount from about 0.1 wt. % to about 10 wt. %, preferably from about 1 wt. % to about 5 wt. %, of the total catalyst.

The catalyst of the present invention is used in the acidic or partially neutralized acidic form. The zeolite or molecular sieve component of the catalyst is typically prepared in the neutral or nonacidic form. In order to obtain the acidic form of the catalyst, the zeolite or molecular sieve component is ion exchanged to produce the ammonium salt form. As a result of calcination, the acid form of the catalyst is produced.

The catalyst in accordance with the present invention can be coked to modify its properties. Coking can be accomplished by contacting the feed with toluene or any other hydrocarbon feed under conditions which include a temperature of about 500° C. to about 700° C. (preferably 500° C. to 600° C.), a pressure of 0 to 1,000 psig, (preferably 50 to 600 psig) a hydrogen to hydrocarbon mole ratio of 0 to 5 (preferably 0 to 1) and a liquid hourly space velocity of 0.1 to 20 (preferably 0.5 to 5). As a result of the coking the catalyst will convert a $C_5-C_9$ hydrocarbon feed in a reforming or aromatization operation under reforming or aromatization conditions to a product which includes xylenes which are enriched in para-xylene.

The catalyst, whether produced by coking or by other methods known in the art as set forth in the various patents showing para-selectivity incorporated above, also has an activity sufficient to provide a BTX yield, based on the $C_6-C_8$ non-aromatics fraction of the feed, of at least about 30% (generally 40% to 75%) on a hydrogen-free basis and at least about 35% (generally 35% to 70%) on a hydrogen inclusive basis. At least about 15% of the BTX is generally xylenes. The para-xylene content of the xylenes will generally be at least about 30% (generally 25% to 80%).

Typical feedstocks which may be utilized with the catalyst preferably include a $C_8$ paraffin component. Substantially any conventional reformer feedstock can be utilized. The feedstock utilized is predominantly paraffinic or olefinic, by which is meant it generally has no more than about 30% aromatics, usually no more than about 20% aromatics. It will generally comprise $C_5-C_9$ hydrocarbons and will have an endpoint of about 300° F. A preferred feed can comprise at least about 20% $C_8$ hydrocarbons and the process then being carried out is primarily a dehydrocyclization process for forming aromatics. When a full boiling range $C_5-C_9$ feedstock is utilized the BTX fraction can be readily separated by conventional extractive distillation. A raffinate is also produced which is useful as a gasoline blending stock. The raffinate will generally have a relatively low octane, which is, however, sufficient so that it can be utilized with an appropriate oxygenated compound such as methyl tertiary butyl ether (MTBE), ethyl tertiary butyl ether (ETBE) or tertiary amyl methyl ether (TAME) to provide a low aromatics content gasoline having an octane value high enough for use in motor vehicles.

A coked catalyst as set forth above can be produced by reacting a catalyst comprising an intermediate pore size molecular sieve support, a platinum group component and a component selected from the group consisting of gallium, zinc, indium, iron, tin and boron with a hydrocarbon until the catalyst becomes coated with coke sufficiently so that it is selectivated so as to be capable of disproportionating toluene to xylenes which are rich in para-xylene. The catalyst, prior to being coked, must have an activity sufficient so that it is capable of converting at least about 30% of a n-octane feed to products other than n-octane at a temperature of 500° C., a liquid hourly space velocity of 0.5 to 2, a pressure of 75 psig and a hydrogen to hydrocarbon mole ratio of 8:1.

In order to improve para-xylene selectivity by coking, the hydrocarbon coking agent is passed over the catalyst at a temperature in the range from about 500° C. to about 600° C. and a pressure in the range from about 50 psig to about 600 psig. Hydrogen may also be added preferably keeping the hydrogen to hydrocarbon molar ratio in the range from 0 to 1, more preferably near 0. The lower hydrogen to hydrocarbon ratios, especially near 0, favor achieving para-xylene selectivity more rapidly. The progress in improving para-xylene selectivity can be measured by passing toluene or a reforming feed over the catalyst at the high temperature coking conditions and measuring the para-xylene content of the $C_8$ aromatics. As the catalyst becomes more para-xylene selective, the para-xylene content of the $C_8$ aromatics will typically increase from its equilibrium value of about 22% to about 60% or higher. In one version of the process, toluene is used as the coking agent and the para-xylene content of the xylenes produced by disproportionation of the toluene is a measure of achieving para-xylene selectivity. This can be done even though the catalysts of the present invention frequently give very low xylene yields from toluene. Ideally, the coking is carried out only to the extent that the catalyst provides sufficient para-xylene selectivity without a major loss in activity as measured by the conversion of n-octane or a reformer feed to xylenes. However, in practice, the coking is frequently accompanied by very significant losses in activity, perhaps down to where the catalyst will convert less than 10% of n-octane under reforming conditions such as 500° C., 50–100 psig, LHSV= 2, and a hydrogen to hydrocarbon ratio of 4.

It has been found that exposing the coked catalyst to a hydrogen atmosphere, either alone or in the presence of the coking agent or other hydrocarbons such as a reformer feedstock, for a sufficient time will result in the catalyst being reactivated to the degree of being capable of converting an n-octane feed to produce at least 30%, preferably 40%, BTX yield on a hydrogen free basis and at least 25%, preferably 35%, BTX yield on a hydrogen inclusive basis from an n-octane feed at a temperature of 500° C., a liquid hourly space velocity of 0.5 to 10, a pressure of 0 to 800 psig and a hydrogen to hydrocarbon molar ratio of 1:1 to 20:1.

Exposing of the coked catalyst to a reducing atmosphere can take place in any of the following manners under the conditions as specified in following:

1) The deactivated catalyst can be reactivated by exposing it to a hydrogen atmosphere at temperatures from about 500° C. to about 600° C. In a preferred case, it can be exposed to a hydrogen flow of 5–100 sccm (standard cubic centimeters per minute) per cubic centimeter of catalyst at 500°–600° C. and 50–200 psig for 10–100 hours. The conditions and the length of time needed to achieve reactivation will depend on the degree of deactivation of the catalyst. For a given state of deactivation, shorter times will be required with the higher temperatures, pressures, and flow rates. It should be recognized that higher hydrogen flow rates will not be harmful as long as the back pressure does not become excessive and the catalyst bed is not physically disrupted. Pressures higher than 200 psig, for example 500–1000 psig, may also be used if it is practical in the equipment being used. The degree of success in reactivation is measured by turning in a feed such as n-octane and measuring the activity and yields. If more activation is needed, the feed can be stopped and the hydrogen treatment continued until the BTX yields from n-octane or a reforming feed reach about 30%, preferably 40%, or higher.

2) The reductive activation can also be accomplished by increasing the hydrogen to hydrocarbon ratio in the reforming process. A preferred version of this is to increase the hydrogen rate, while holding the feed rate constant, until the catalyst begins to reactivate, and then holding under these conditions or continuing to increase the hydrogen rate until activity is recovered. To accomplish the activation, the hydrogen to hydrocarbon ratio may be increased up to levels of 10–100:1. Even higher hydrogen to hydrocarbon ratios do no harm as long as the back pressure does not become excessive and the catalyst bed is not physically disturbed. This method of activation is especially useful when the activation described under 1) above is not sustained for a practical length of time. However, the reductive activation by increasing the hydrogen to hydrocarbon ratio during reforming may also be used in place of 1).

The reductive activation can also be accomplished by hydrogen treatments during the coking step for increasing para-xylene selectivity. In a preferred version of this, the coking by hydrocarbon is periodically interrupted for hydrogen treatments at the coking temperature. For example, toluene coking at about 600° C. can be carried out until the para-xylene selectivity reaches 30%, preferably 40%, or higher (expressed as % of total xylenes). The toluene is turned off and the catalyst is treated with hydrogen at 600° C., typically for 10 to 100 hours. As a result of this high temperature hydrogen treatment of the partially selectivated catalyst, the para-xylene selectivity may temporarily decrease but will be rapidly regained when the toluene feed is restarted at 600° C. The alternating of toluene coking with hydrogen treatment may be repeated more than once, but one time is typically satisfactory.

Substantially any catalyst which is para-selective for toluene disproportionation can be used in the practice of the invention. For example, any catalyst which can be coked to provide para-selectivity during a toluene disproportionation process can be used in the process of the present invention. Examples of such catalysts are found in U.S. Pat. Nos. 4,117,026 and 4,097,543 of Haag and Olson, both of which are incorporated herein in their entireties by reference. The coked catalysts of the present invention are not "para-selective" as that term is known in the art (although they do exhibit para-selectivity) but are instead better considered as being para-modified by first being coked to produce para-selectivity and then being reduced so as to be useful for selective reforming/aromatization to form a para-xylene enriched reformate/aromatization product. In general, the term "para-modified" as used herein means that the catalyst, when used in accordance with the present invention, will produce a BTX fraction in which at least 30% of the xylenes constitutes para-xylene. Indeed, as is shown in the examples well over 60% of the $C_8$ aromatics produced can be para-xylene. Attaining such a higher percentage of para-xylene is generally desirable. Other para-selective catalysts can also be utilized, for example, catalysts as set forth in previously mentioned U.S. Pat. Nos. 4,011,276; 4,016,219; 4,052,476; 4,029,716; 4,067,919; 4,097,543; 4,098,837; 4,127,616; 4,160,788; 4,182,923; 4,361,713; 4,365,104; 4,367,359; 4,370,508; 4,308,685 and 4,384,155, all of which have previously been incorporated by reference.

The use of large crystal size zeolites having a minimum crystal dimension of greater than about 0.5 micron, generally in the approximate range of 1–20 microns and particularly 1–6 microns is generally preferred as adding to the para-selectivity.

In assessment of zeolite crystal size, conventional scanning electron microscopy (SEM) techniques can be used, the minimum crystal dimension of a given crystal being taken as the dimension of reference. The crystalline aluminosilicate zeolites used in the present invention in substantial proportion are essentially characterized by a minimum crystal dimension of greater than about 0.5 micron. It is contemplated that the amount of zeolite of such crystal size will be such as to exert a directive influence in the desired selective production of paradialkyl substituted benzenes. Generally, the amount of zeolite of such crystal size will be present in predominate proportion, i.e., in an amount exceeding 50 weight percent, and preferably may constitute up to 100 weight percent of the total zeolite employed.

The coked crystalline aluminosilicate zeolites employed, particularly those having a minimum crystal dimension of greater than about 0.5 micron, have undergone modification prior to use by selective precoking thereof to deposit at least about 1 weight percent and generally between about 2 and about 40 weight percent of coke thereon, based on the weight of total catalyst. If the zeolite is employed in substantially pure form or in combination with a low coking binder, such as silica, then the weight percent of coke deposited is generally in the range of 2 to 20 weight percent. When the zeolite is combined with a binder of high coking tendencies, such as alumina, coke deposition content of the total catalyst, prior to its being exposed to a reducing environment, is in the approximate range of 10 to 40 weight percent. Precoking can be accomplished by contacting the catalyst with a hydrocarbon charge, e.g., toluene, under high severity conditions at a reduced hydrogen to hydrocarbon concentration, i.e., 0 to 1 mole ratio of hydrogen to hydrocarbon for a sufficient time to deposit the desired amount of coke thereon.

Following coking, if necessary to recover activity, the catalyst is exposed to a reducing atmosphere as described elsewhere herein thereby reducing the coke content to provide the para-modified catalyst. The exposure to the reducing atmosphere is continued until the coked catalyst activity for converting n-octane to other products has risen to at least 30 wt.% but is not continued to an extent which would significantly reduce the para-selectivity of the catalyst.

The ZSM-5 silicalite structure is the preferred zeolite for the reforming/aromatization/dehydrocyclization reaction. The ZSM-5 preferably has a silica to alumina mole ratio of between 10 and 20,000, generally between 10 and 1000. Where the ZSM-5 is a Ga ZSM-5 with Ga in or out of the zeolite framework, the preferred $SiO_2/Ga_2O_3$ mole ratio is in the range from about 10 to about 1,000.

The process described herein is generally carried out as a semi-continuous or continuous operation utilizing a fixed or moving bed catalyst system.

In accordance with the method of reforming or aromatizing of the invention a hydrocarbon feedstock is contacted under reforming or aromatization conditions with a catalyst as defined above with the catalyst having been exposed to a hydrogen atmosphere following coking as described above.

The process of the present invention can suitably be carried out under conditions which include a pressure from about 0 to about 800 psig, preferably from about 50 to about 400 psig, a liquid hourly space velocity of 0.5 to 10, preferably 0.5 to 5 and more preferably 1 to 4, a hydrogen to hydrocarbon mole ratio of 1 to 20, preferably 2 to 10. The conditions are generally adjusted so as to produce a BTX yield of about 40% on a hydrogen-free basis.

In accordance with one embodiment of the present invention the catalyst is used in the reforming operation followed by the use of a second stage non-acidic aromatization catalyst which will increase aromatics yield. The catalyst for increasing aromatics generation may be based on an inorganic oxide support, e.g., alumina or a molecular sieve such as L-zeolite or silicalite, with an inorganic oxide binder. Preferred catalysts for increasing aromatization yield include catalysts comprising platinum on non-acidic forms of beta-zeolite, ZSM-5, silicalite and L-zeolite. Other well-known aromatization catalysts typically contain a catalytic metal, e.g., a platinum group metal such as platinum, disposed on any of a plethora of natural and man-made crystalline aluminosilicates. Other promoter metals, e.g., rhenium or tin, can also be included. The preferred catalyst for increasing aromatics yield is Pt on L-zeolite. L-zeolite suitable for this purpose can be made as set forth in U.S. Pat. No. 4,634,518 issued Jan. 6, 1987 to W. C. Buss and T. R. Hughes which is hereby incorporated herein by reference. A more preferred form of L-zeolite catalyst for the second stage is set forth in commonly assigned U.S. patent application Ser. No. 08/151,814 of B. Mulaskey, et al, filed Nov. 15, 1993, the disclosure of which is incorporated herein by reference.

The invention will be better understood by reference to the following experimental examples.

EXAMPLE 1

Preparation of Pt/Ga HZSM-5

Ga ZSM-5 was prepared with a $SiO_2/Ga_2O_3$ ratio of approximately 50. The sodium salt of the Ga ZSM-5 was ion exchanged with $Pt(NH_3)_4(NO_3)_2$ in aqueous ammonia at pH 9. The catalyst was dried at 121° C. and calcined at 288° C. to give, Pt/Ga HZSM-5. The amounts used calculate as providing 0.5% Pt by weight on Ga HZSM-5.

increased to 61% but the toluene conversion had dropped to 11%.

After the high temperature toluene treatment, the xylenes from reforming n-octane at 510° C. had a para-xylene content of 73%, well above equilibrium, but the feed conversion had dropped to 4%. The deactivated catalyst was hydrogen activated by turning the feed off and running hydrogen-only at 510° C. for periods of 0.5 to several days. As a result of these hydrogen activation treatments, the activity was increased to give feed conversions of 70+% while the para-xylene selectivity was maintained well above equilibrium. However, under the conditions used, the 10 activity fell rapidly over a period of a few hours after each hydrogen activation. As shown in Table 1 for the HYDROGEN ACTIVATED case, the conversion dropped from 71% to 24% in 30 hours. The catalyst activity was stabilized by hydrogen activation in combination with raising the hydrogen to feed ratio. As Table 1 shows, the conversion was stabilized for more than 100 hours at 70+% with a $C_8$ aromatics yield of 15–18% and a para-xylene content of 90% of the xylenes. A comparison with the fresh catalyst results in Table 1 shows that the coking and hydrogen activation process of the present invention has increased both the $C_8$ aromatics yield and the para-xylene content.

TABLE 1

| STATUS | FRESH | TOLUENE COKING | COKED | HYDROGEN ACTIVATED | | HYDROGEN STABILIZED | |
|---|---|---|---|---|---|---|---|
| FEED | N—$C_8$ | TOLUENE | N—$C_8$ | N—$C_8$ | | N—$C_8$ | |
| LHSV | 2 | 2 | 2 | 2 | | 2 | |
| $H_2$/FEED | 7.8 | 0 | 3.9 | 3.9 | | 7.8 | |
| TEMP., °C. | 427 | 593 | 510 | 510 | | 510 | |
| P, Psig | 50 | 62   80 | 70 | 70   70 | 85 | 82 | |
| RUN HOURS | 100 | 522  546 | 738 | 1340  1370 | 1777 | 1893 | |
| % CONVERSION | 100 | 29   11 | 4 | 71   24 | 70 | 72 | |
| % YIELD $C_8$ AROMATICS | 4 | 6.6   5 | 0.75 | 23   9 | 15 | 18 | |
| PX, % of $C_8$ AROMATICS | 23 | 25   52 | 61 | 58   69 | 77 | 77 | |
| PX, % of XYLENES | 23 | 25   61 | 73 | 66   83 | 90 | 90 | |

EXAMPLE 2

PARA-XYLENE SELECTIVE REFORMING OF N-OCTANE

This example illustrates coking and hydrogen activation procedures which provide a stabilized high conversion and high yield catalyst which is also selective for producing para-xylene at above equilibrium concentrations. It is especially surprising that the Pt containing catalyst can be coked to give a high para-xylene selectivity and then hydrogen activated to give high conversions and high aromatic yields without loss of para-xylene selectivity.

About 0.5 cc of the Pt/Ga HZSM-5 from Example 1 was placed in a down-flow micro-reactor and reduced with hydrogen at about 510° C. Hydrogen and n-octane were passed over the catalyst at 427° C. and the products were analyzed by gas chromatography using an in-line sample valve. The results of this analysis and other analyses taken during the run are given in Table 1. As shown in Table 1 for the sample at 427° C., the $C_8$ aromatics (xylenes+ethylbenzene) yield was very low and the para-xylene content was approximately at equilibrium.

The catalyst was subjected to high temperature coking conditions using toluene and decreasing amounts of hydrogen. After 25 hours at about 593° C. with toluene and no hydrogen, the para-xylene content of the xylenes had

EXAMPLE 3

COKING WITHOUT DEACTIVATION

This example illustrates the process where the high temperature coking is accomplished without deactivation.

About 0.5 cc of the Pt/Ga HZSM-5 from Example 1 was placed in a down-flow micro-reactor and reduced with hydrogen at about 510° C. as in Example 2. The catalyst was subjected to high temperature toluene treatment at 593° C. with no hydrogen in order to increase para-xylene selectivity. After about 24 hours, the toluene feed was turned off and the catalyst was held at 593° C. for 64 hours with only nitrogen flowing. The high temperature toluene treatment was then continued until the para-xylene content of the $C_8$ aromatics had increased to 60%. The feed was changed to n-octane/hydrogen and the run was continued for a time at 593° C. and then at 510° C. The analytical results for samples taken during this run are summarized in Table 2. As the results in Table 2 show, the coked catalyst gave 99% feed conversion and para-xylene concentrations substantially above equilibrium. This illustrates that controlled high temperature treatment of the catalyst with and without hydrocarbon feed can be used to achieve para-xylene selective reforming performance without loss of catalyst activity.

TABLE 2

| STATUS | TOLUENE COKING | N$_2$ TREAT | TOLUENE COKING | | N—C$_8$ REFORMING | | |
|---|---|---|---|---|---|---|---|
| FEED | TOLUENE | NONE | TOLUENE | | N—C$_8$ | N—C$_8$ | |
| LHSV | 1 | 0 | 1 | | 1 | 1 | |
| H$_2$/FEED | 0 | 0 | 0 | | 8.3 | 8.3 | |
| TEMP., °C. | 593 | 593 | 593 | | 593 | 510 | |
| P, Psig | 65 | 62 | 62 | 62 | 62 | 63 | 62 |
| RUN HOURS | 196 | 219 | 288 | 311 | 335 | 357 | 390 |
| CONVERSION | 4.5 | 8 | 8.4 | 7 | 100 | 99 | 99 |
| % YIELD C$_8$ AROMATICS | 1 | 0.7 | 0.4 | 0.5 | 34 | 28 | 33 |
| PX, % of C$_8$ AROMATICS | 28 | 40 | 50 | 60 | 60 | 68 | 68 |

EXAMPLE 4

HYDROGEN TREATMENT TO IMPROVE AROMATICS YIELD

This example illustrates the use of the hydrogen treatment to activate the catalyst for the production of aromatics. This example is a continuation of the catalyst test described in Example 3. At about 390 hours of the run described in Example 3, the feed was turned off and the catalyst was treated with hydrogen for more than 60 hours. The n-octane feed was then turned on and the test continued. As the analytical results in Table 3 show, the hydrogen treatment resulted in increased yield of the aromatics.

The catalyst is the same one used in Examples 3 and 4. The catalyst test described in Example 4 was continued with a change from n-octane feed to the feed described in Table 4 at about 530 run hours. The test was continued for more than 100 hours with BTX yields of 42+%, C$_8$ aromatics yields of 18+% and para-xylene contents of 43+% of the C$_8$ aromatics. The results are summarized in Table 5.

TABLE 3

| STATUS | N—C$_8$ REFORMING | | | HYDROGEN ONLY | N—C$_8$ REFORMING | |
|---|---|---|---|---|---|---|
| FEED | N—C$_8$ | N—C$_8$ | | H$_2$ | N—C$_8$ | |
| LHSV | 1 | 1 | | | 1 | |
| H$_2$/FEED | 8.3 | 8.3 | | | 8.3 | |
| TEMP., °C. | 593 | 510 | | 510 | 510 | |
| P, psig | 62 | 63 | 62 | 62 | 62 | 62 |
| RUN HOURS | 335 | 357 | 390 | | 462 | 527 |
| % CONVERSION | 100 | 99 | 99 | | 99.9 | 99.9 |
| % YIELD C$_8$ AROMATICS | 34 | 28 | 33 | | 44 | 44 |
| PX, % of C$_8$ AROMATICS | 60 | 68 | 68 | | 70 | 66 |
| % YIELD BTX | 41 | 30 | 35 | | 49 | 49 |

EXAMPLE 5

REFORMING A BROAD RANGE FEED

This example illustrates the use of the catalyst and process of the present invention to achieve para-xylene selective reforming with a broad range feed. The feed was a 149° C. end point feed with the approximate composition by carbon number shown in Table 4. The aromatics content was less than 10%.

TABLE 4

| Carbon Number | Weight Percent |
|---|---|
| C$_4$— | 0.45 |
| C$_5$ | 1.99 |
| C$_6$ | 14.26 |
| C$_7$ | 46.93 |
| C$_8$ | 32.04 |
| C$_9$+ | 4.35 |

TABLE 5

| STATUS | BROAD RANGE FEED REFORMING | |
|---|---|---|
| FEED | DESCRIBED IN TABLE 4 | |
| LHSV | 1 | |
| HYDROGEN/FEED RATIO | 7.2 | |
| TEMPERATURE, °C. | 510 | |
| P, psig | 62 | 70 |
| RUN HOURS | 532 | 677 |
| WT. % BTX YIELD | 45.5 | 42 |
| WT. % C$_8$ AROMATICS YIELD | 21 | 18.5 |
| PX as % of C$_8$ AROMATICS | 43 | 50 |

EXAMPLE 6

PROCESS WITH ADD-ON CATALYST

This example illustrates the process of the present invention when used with two catalysts in sequence to increase aromatics yield. The catalyst test described in Example 5 was continued with the addition of a non-acidic Pt on L zeolite as an add-on catalyst. The non-acidic Pt on L zeolite was prepared as was the catalyst described in U.S. Pat. No. 4,634,518 issued Jan. 6, 1987 to W. C. Buss and T. R. Hughes. The Pt on L catalyst was downstream from the coked and hydrogen activated Pt/Ga HZSM-5 of Examples 3, 4, and 5. The feed was the same as that used in Example 5. The Pt/L catalyst was held at 455° C. with the Pt/Ga HZSM-5 at 510° C. As shown in Table 6, the addition of the Pt/L catalyst resulted in an increase in the BTX yield from the 42–45.5% shown in Table 5 to 51+% shown in Table 6. The para-xylene content in the $C_8$ aromatics was also maintained above equilibrium levels.

TABLE 6

| STATUS | Dual Catalysts Pt/Ga HZSM-5 over Pt/L | |
| --- | --- | --- |
| FEED | DESCRIBED IN TABLE 4 | |
| LHSV | 0.5 | |
| HYDROGEN/FEED RATIO | 7.2 | |
| TEMPERATURE, °C. | 510/455[1] | |
| P, psig | 69 | 69 |
| RUN HOURS | 840 | 892 |
| WT. % BTX YIELD | 51.2 | 51.5 |
| PX as % of $C_8$ AROMATICS | 34 | 34 |

[1]Pt/Ga HZSM-5 @ 510° C. and Pt/L @ 455° C.

EXAMPLE 7

DUAL CATALYST PROCESS

This example illustrates the present invention when implemented with two catalysts in the same reactor bed. A two-staged catalyst bed was prepared with the catalyst from Example 1 as the first stage above a Pt/L-zeolite second stage catalyst. This is similar to Example 6 except that both catalysts were in the same reactor and both catalysts were exposed to the same on-stream history. The second stage catalyst was also prepared as was the catalyst described in U.S. Pat. No. 4,634,518 issued on Jan. 6, 1987 to W. C. Buss and T. R. Hughes. The catalysts were pretreated with hydrogen at 510° C. The test was started with hydrogen/n-octane feed. The analytical results for samples taken during the run are summarized in FIG. 1.

With the fresh catalysts, the feed was 100% converted at 510° C. but no xylenes were produced. The high temperature coking of the catalysts at 593° C. was interspersed with periods of hydrogen-only treatments for a period of time spanning more than 300 hours. The coke buildup was accompanied by an increase in back pressure. The hydrogen-only treatments helped to keep the back pressure from becoming excessive but also may have helped avoid excessive catalyst deactivation during coking. After coking and hydrogen treatments, as shown in FIG. 1, the catalysts gave high feed conversions, high aromatics yields, and substantially higher than equilibrium contents of para-xylene in the $C_8$ aromatics.

EXAMPLE 8

DUAL CATALYST WITH BROAD RANGE FEED

Figure 2:
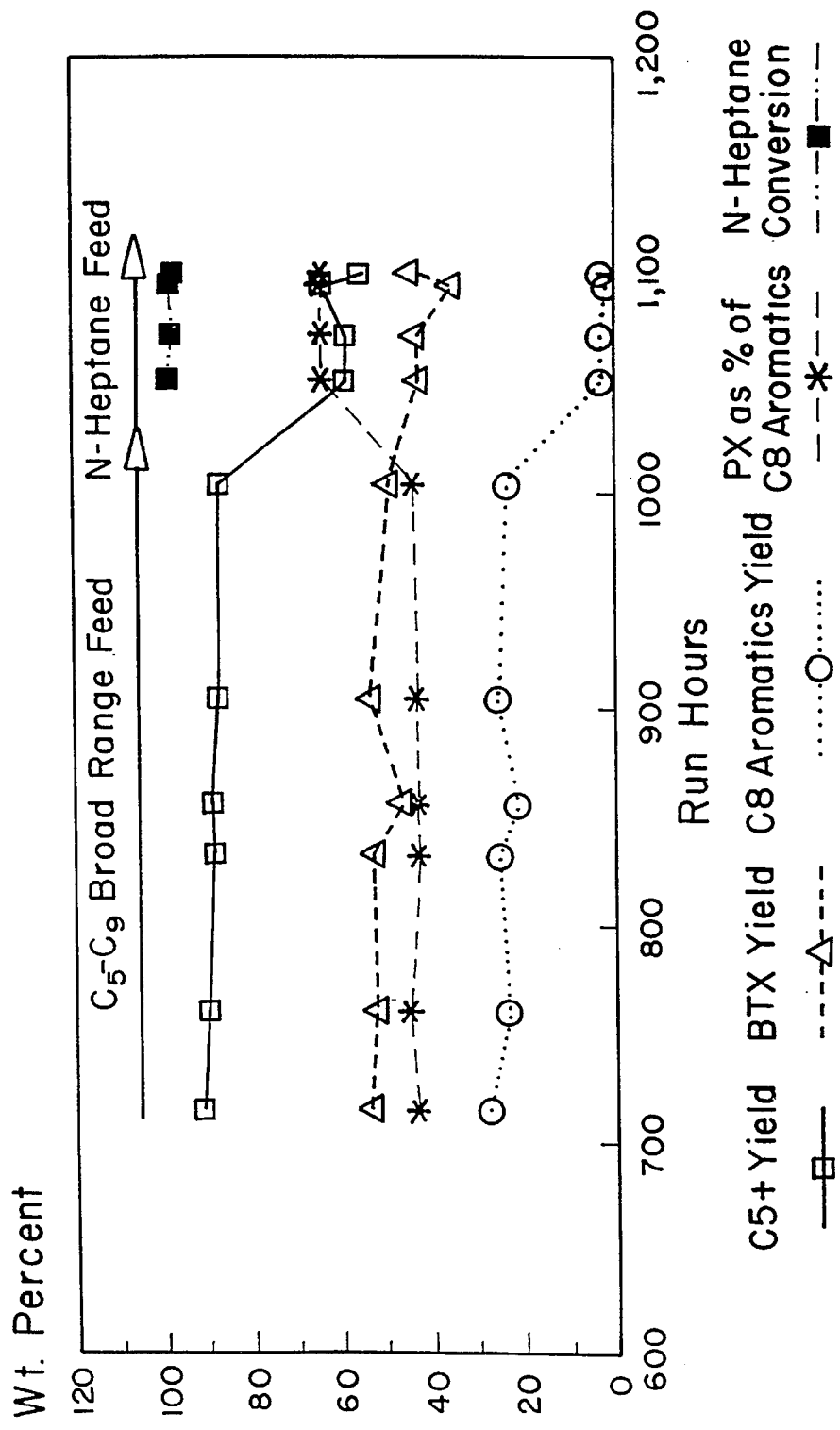
FIG. 2 illustrates experimental results as described in Example 8.

This example illustrates the present invention when implemented with two catalysts in the same reactor bed and with a broad range feed. The catalyst test described in Example 7 and FIG. 1 was continued with the broad boiling range feed described in Table 4 and Example 5. FIG. 2 shows the yield results after the test run had lined out at about 700 hours. As FIG. 2 shows, the catalysts and process of the present invention gave high aromatics yields (50+% BTX and 20+% $C_8$ aromatics) and higher than equilibrium levels of para-xylene (40+%) in the $C_8$ aromatics. FIG. 2 also shows that the high yield and selectivity was maintained for at least about 300 hours with no significant change in performance.

EXAMPLE 9

DUAL CATALYST WITH N-HEPTANE FEED

This example illustrates that the catalysts and process of the present invention does not produce significant levels of para-xylene or other xylenes by the reforming and toluene disproportionation pathway. The low xylene yields obtained from toluene disproportionation in Example 2 and Table 1 as well as Example 3 and Table 2 have already shown that the catalysts of the present invention are not suitable as toluene disproportionation catalysts. The present example reinforces this point by showing that the catalysts and process of the present invention do not produce xylenes to a significant extent from the aromatization of feed components to toluene followed by toluene disproportionation to xylenes and benzene.

The catalyst test in Example 8 was continued with a change of feed to n-heptane at about 1000 hours run time. As FIG. 2 shows, the change to n-heptane feed resulted in a sudden severe drop in $C_8$ aromatics yield. More details are provided in Table 7. Table 7 gives selected characteristic results that were obtained with the three different feeds which were used in Examples 7, 8, and 9. As Table 7 shows, n-heptane gave the highest yields of toluene and the lowest yields of xylenes.

TABLE 7

| STATUS | N—$C_8$ REFORMING | $C_{5-9}$ REFORMING | N-HEPTANE REFORMING | |
| --- | --- | --- | --- | --- |
| FEED | N-OCTANE | BROAD RANGE | N-HEPTANE | |
| LHSV | 0.5 | 0.5 | 0.5 | |
| $H_2$/FEED | 8.3 | 7.2 | 7.5 | |
| TEMP., °C. | 510 | 510 | 510 | |
| P, psig | 130 | 130 | 130 | |
| RUN HOURS | 692 | 928 | 1072 | 1100 |
| % CONVERSION | 98.5 | | 98.2 | 98.1 |
| % YIELD TOLUENE | 6.1 | 23.7 | 39 | 41 |
| % YIELD XYLENES | 35 | 19.2 | 2.6 | 2.64 |
| Px, as % of XYLENES | 85.8 | 54.4 | 72.6 | 73.1 |

Industrial Applicability

The present invention is useful for the production of aromatics, most particularly of para-xylene. It can also produce a gasoline blending stock along with the para-xylene enriched BTX fraction.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

That which is claimed is:

1. A method of reforming or aromatizing a $C_5$–$C_9$ predominantly paraffinic or olefinic hydrocarbon feedstock to produce a reformate which is enriched in para-xylene, comprising:

contacting the feedstock under reforming or aromatization conditions with a para-modified catalyst comprising an intermediate pore size molecular sieve support, a platinum group component and a component selected from the group consisting of gallium, zinc, indium, iron, tin and boron to produce a hydrocarbon product, the para-modified catalyst having an activity sufficient to produce a yield of at least about 30%, on a hydrogen free basis, based on a $C_6$–$C_8$ non-aromatics portion of the feedstock, of benzene-toluene-xylenes-ethyl benzene (BTX) from a $C_5$–$C_9$ predominantly paraffinic or olefinic hydrocarbon feedstock, the $C_6$–$C_8$ non-aromatics portion comprising at least about 30% of the feedstock, at least about 15% of the BTX consisting of xylenes, with the xylenes being at least about 30% para-xylene.

2. A method as set forth in claim 1, wherein the para-modified catalyst has been coked sufficiently to be capable of converting toluene to xylenes which are enriched in para-xylene.

3. A method as set forth in claim 2, wherein following coking the para-modified catalyst has been exposed to a hydrogen containing atmosphere for a time sufficient so that it is capable of converting at least 30% of an n-octane feed to products other than n-octane at a temperature of 500° C., a liquid hourly space velocity of 0.5, a pressure of 75 psig and a hydrogen to hydrocarbon molar ratio of 10:1.

4. A method as set forth in claim 3, wherein the intermediate pore size molecular sieve support is ZSM-5, ZSM-11, ZSM-12, ZSM-21, ZSM-22, ZSM-23, ZSM-35, ZSM-38, ZSM-48, ZSM-57, SSZ-23, SSZ-25, SSZ-32, SAPO-11, SAPO-31, SAPO-41, MAPO-11 or MAPO-31.

5. A method as set forth in claim 4, wherein the platinum group component is platinum in an amount within a range from 0.1 to 5 weight percent based on the intermediate pore size molecular sieve support.

6. A method as set forth in claim 5, wherein the additional component is gallium in an amount within a range from 0.1 to 10 weight percent based on the intermediate pore size molecular sieve support.

7. A method as set forth in claim 6, wherein the intermediate pore size molecular sieve support comprises ZSM-5 having a silica to alumina mole ratio which falls within a range from 10:1 to 1,000:1.

8. A method as set forth in claim 1, further including:

separating the reformate into a BTX containing fraction and a BTX-free raffinate fraction.

9. A method as set forth in claim 1, wherein the feedstock contains no more than about 30% aromatics.

10. A method as set forth in claim 1, further including:

contacting the hydrocarbon product in a subsequent aromatization stage under reforming or aromatization conditions with an aromatization catalyst comprising a platinum group component on a non-acidic inorganic oxide support.

11. A method as set forth in claim 10, wherein the para-modified catalyst has been coked sufficiently to be capable of converting toluene to xylenes which are enriched in para-xylene.

12. A method as set forth in claim 11, wherein following coking the para-modified catalyst has been exposed to a hydrogen containing atmosphere for a time sufficient so that it is capable of converting at least 30% of an n-octane feed to products other than n-octane at a temperature of 500° C., a liquid hourly space velocity of 0.5, a pressure of 75 psig and a hydrogen to hydrocarbon molar ratio of 10:1.

13. A method as set forth in claim 12, wherein the intermediate pore size molecular sieve support is ZSM-5, ZSM-11, ZSM-12, ZSM-21, ZSM-22, ZSM-23, ZSM-35, ZSM-38, ZSM-48, ZSM-57, SSZ-23, SSZ-25, SSZ-32, SAPO-11, SAPO-31, SAPO-41, MAPO-11 or MAPO-31.

14. A method as set forth in claim 13, wherein the platinum group component is platinum in an amount within a range from 0.1 to 5 weight percent based on the intermediate pore size molecular sieve support.

15. A method as set forth in claim 14, wherein the additional component is gallium in an amount within a range from 0.1 to 10 weight percent based on the intermediate pore size molecular sieve support.

16. A method as set forth in claim 15, wherein the intermediate pore size molecular sieve support comprises ZSM-5 having a silica to alumina mole ratio which falls within a range from 10:1 to 1,000:1.

17. A method as set forth in claim 10, further including:

separating the reformate into a BTX containing fraction and a BTX-free raffinate fraction.

18. A method as set forth in claim 10, wherein the feedstock contains no more than about 30% aromatics.

* * * * *